United States Patent [19]

Garsky

[11] 4,231,925

[45] Nov. 4, 1980

[54] PENTAPEPTIDES WITH ANALGESIC ACTIVITY ON PERIPHERAL ADMINISTRATION

[75] Inventor: Victor M. Garsky, Radnor, Pa.

[73] Assignee: American Home Products Corporation, New York, N.Y.

[21] Appl. No.: 59,911

[22] Filed: Jul. 23, 1979

[51] Int. Cl.$^3$ .................. C07C 103/52; A61K 37/00
[52] U.S. Cl. ......................... 260/112.5 R; 424/177
[58] Field of Search ............. 424/177; 260/112.5 R

[56] References Cited

U.S. PATENT DOCUMENTS

| | | | |
|---|---|---|---|
| 4,103,005 | 7/1978 | Li | 424/177 |
| 4,148,786 | 4/1979 | Sarantakis | 424/177 |

*Primary Examiner*—Delbert R. Phillips
*Attorney, Agent, or Firm*—Arthur G. Seifert

[57] ABSTRACT

Disclosed are substituted-(D-Met$^2$, D-Ser$^5$)-enkephalins which elicit analgesic activity when administered peripherally.

6 Claims, No Drawings

PENTAPEPTIDES WITH ANALGESIC ACTIVITY ON PERIPHERAL ADMINISTRATION

The compounds of the invention are substituted-(D-Met², D-Ser⁵) enkephalins which exhibit analgesic activity when administered peripherally.

BACKGROUND OF THE INVENTION

The search for a natural opiate receptor agonist in the brain led to the isolation of a low molecular weight peptide called "enkephalin" and to its identification by Hughes et al. as a mixture of two pentapeptides: H—Tyr—Gly—Gly—Phe—Met—OH (methionine enkephalin) and H—Tyr—Gly—Gly—Phe—Leu—OH (leucine enkephalin). The opiate receptor agonist properties of these pentapeptides were demonstrated by their ability to block electrically evoked contractions of mouse vas deferens and guinea pig ileum and by their ability to inhibit the stereospecific receptor binding of the opiate antagonist 3H-naloxone in brain homogenates, which are standard opiate receptor agonist properties of morphine.

It has been proposed that enkephalin receptors in the brain may be sites at which morphine-like drugs exert their analgesic effects. It is further proposed that the enkephalins may be the natural modulators or transmitters in the brain's systems for pain suppression or analgesia. The analgesic effect of methionine-enkephalin (Met-enkephalin) and leucine-enkephalin (Leu-enkephalin) was, indeed, reported by Belluzzi et al. in Nature, 260, 625–6 (1976). Their measurements of the analgesic effects of the two enkephalins injected intraventricularly into the rat brain in the tail-flick procedure showed that they produced analgesia equivalent to morphine, albeit at doses of 10–20 times that of morphine and for short intervals (10–12 minutes compared to an hour or more for morphine). Belluzzi et al. also found this analgesia to be reversible by the administration of naloxone, further demonstrating the opiate-like analgesic properties of the two natural enkephalins.

However, Met-enkephalin and Leu-enkephalin are virtually inactive when administered systemically (e.g. subcutaneously or intravenously), as reported by Frederickson et al. in *Opiates and Endogenous Opioid Peptides*, H. Kosterlitz, Ed., pp. 239–246, Elsevier/North-Holland, Biomedical Press, Amsterdam (1976). Strong evidence indicates that the reason for this lack of systemic activity and the short duration of intraventricular activity of the two enkephalins is the rapid enzymatic breakdown of the two peptides, particular at the Tyr¹—Gly² peptide bond. For example, Chang et al., Life Sciences, 18, 1473 (1976), demonstrated that preincubation of the enkephalins at 34° C. with brain membrane preparations results in a 50–100 percent loss of potency in the receptor assay. C. B. Pert et al., *Kosterlitz, supra*, at pp. 79–86, found that substitution of D-Ala² for Gly² of Met-enkephalin protected against degradation and produced a more potent, long-acting analgesic. Additionally, Hambrook et al., Nature, 262, 782–783 (1976), found that Met-enkephalin and Leu-enkephalin were, in fact, broken down in both rat and human blood plasma. It has also been suggested that poor transportation of the enkephalins across the blood-brain barrier may be partially responsible for their lack of analgesic activity after systemic administration.

Of further significance to the physiology of the enkephalins is the observation that Met-enkephalin has the same peptide sequence as the N-terminal portion of α-, δ-, and β-endorphin, which, in turn, corresponds to the C-terminal sequence (61–91) of β-lipotropin. β-Lipotropin is found in large concentrations in the pituitary gland and in much lower concentrations in the brain. This relationship—coupled with the finding that the endorphins and β-lipotropin also exhibit morphine-like properties in various test systems—has led to the suggestion that Met-enkephalin is a natural breakdown product of β-lipotropin.

The various reports presented in *Opiates and Endogenous Opioid Peptides*, Kosterlitz, Ed., supra, are reviewed by Iverson and Dingledine in Nature, 262, 738–739 (1976). The role of the enkephalins in neurotransmission and analgesia is examined by Robert C. A. Frederickson in "Enkephalin Peptapeptides—a review of current evidence for a physiological role in vertebrate neurotransmission", Life Sciences, 21, 23–42 (1977). In a 1978 review, "Endogenous peptides and analgesia", Ann. Rev. Pharmacol. Toxicol., 18, 189–204, Lars Terenius further examines the endorphins (including the enkephalins) and pain mechanisms.

In order to obtain an enkephalin-like pentapeptide with analgesic activity upon peripheral (e.g. subcutaneous, intravenous, or oral) administration, numerous analogs have been made in which one or more of the amino acids in enkephalin have been replaced by another amino acid, removed, or structurally modified. For example, Belgian Pat. No. 853,448 to Imperial Chemical Industries, Limited, shows the compound (D-Met², Leu⁵) enkephalin, methyl ester. U.S. Pat. No. 4,128,541 to Sarantakis discloses (Ser⁵)-enkephalin eliciting analgesic activity upon administration in the rat lateral brain ventricle. Dutta et al., Life Sciences, 21, 559–562 (1977), report that (D-Met², Leu⁵) enkephalin, methyl ester shows strong opiate receptor agonist activity in the electrically stimulated guinea pig ileum model. Dutta et al., Id., at p. 560, also point out the lack of correlation between the standard in vitro opiate-receptor binding assays and the in vivo analgesic activity exhibited by some 200 enkephalin analogs which they investigated. Roemer et al., Nature, 268, 547–549 (1977), report that (D-Ala², Met(O)⁵)-enkephalin and (D-Ala², Me-Phe⁴, Met(0)⁵)-enkephalin elicited analgesic activity after oral administration. In separate papers, S. Bajusz and J. I. Szekely and their co-workers report that (D-Met², Pro⁵)-enkephalin amide elicits analgesic activity when administered intracerebroventricularly, intravenously, or subcutaneously. [See Bajusz et al., Acta Biochem. et Biophys. Acad. Sci. Hung., II(1), 305–309 (1976) and Szekely et al., European Journal of Pharmacology, 43, 293–294 (1977)]. This compound is also disclosed in Derwent Abstract No. 19638A which is an abstract of Belgian Pat. No. 858,453 to Richter Gedeon Vegy.

DETAILED DESCRIPTION OF THE INVENTION

This invention comprises pentapeptides having the formula:

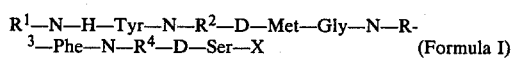

R¹—N—H—Tyr—N—R²—D—Met—Gly—N—R³—Phe—N—R⁴—D—Ser—X     (Formula I)

wherein

R¹ is hydrogen, methyl, ethyl, propyl, 2-methyl-2-pentenyl, 2-methyl-1-pentenyl, methylcyclopropyl, methylcyclobutyl;

$R^2$, $R^3$, and $R^4$ are, independently, hydrogen or methyl; and

X is an amino group, $OR^5$, or —$CH_2OR^5$ where $R^5$ is hydrogen or an alkyl group containing 1 to 6 carbon atoms;

or a pharmaceutically acceptable salt thereof.

All chiral amino acids in the above formula and throughout this specification and claims are in the L- or natural configuration unless otherwise indicated.

Preferred compounds of the invention are those in which $R^3$ is methyl. Particularly preferred are such compounds in which $R^2$ and $R^4$ are hydrogen. Also preferred are those compounds in which $R^1$ is other than hydrogen. Particularly preferred compounds of the latter group are those in which $R_1$ is methyl.

A further group of preferred compounds are those in which X is an amino group or —$OR^5$ where $R^5$ is methyl.

Thus the amino acid sequence of the pentapeptides of the invention differs from Met-enkephalin and Leu-enkephalin in two respects; viz., L-$Gly^2$ is replaced by D-$Met^2$ and L-$Met^5$ or L-$Leu^5$ is replaced by D-$Ser^5$. Additionally, the preferred compounds of the invention have substituents on the amino group of the N-terminal tyrosine, on the amino group of the phenylalanine in the four position, and on the carboxyl group of the C-terminal D-serine, further distinguishing such compounds from met-enkephalin and Leu-enkephalin.

The pentapeptides of Formula I, or a non-toxic salt thereof, exert an analgesic effect as demonstrated after peripheral (e.g. subcutaneous) administration in mice according to the phenylbenzoquinone-induced writhing test procedure. Additionally, the compounds of Formula I bind to rat brain opiate receptors with on the order of ten times the affinity of morphine, as demonstrated in a standard opiate-receptor binding assay.

The pentapeptides of Formula I may be prepared by solid phase synthesis. In such solid phase synthesis, the C-terminal α-amino acid of the polypeptide is first protected at the α-amino position and on any reaction side-chain position, and then linked to a resin support via an amide or an ester linkage to an appropriate linking group on the support. The resin support normally utilized is a polystyrene resin cross-linked with 1-2% divinylbenzene. In order to obtain the amide linkage, a benzhydrylamine linking group is formed on the resin. In order to obtain the ester linkage, a chloromethyl or hydroxymethyl linking group is formed on the resin.

The benzyhydrylamine resin may be prepared by the benzoylation of the cross-linked polystyrene resin, followed by a Leuckart reduction of the resulting phenylketo group using formic acid and ammonium formate and, thereafter, hydrolysis of the resulting intermediate benzhydrylformylamine with concentrated hydrochloric acid. This and other preparative routes are described by Orlowski et al., J. Org. Chem., 41, 3701 (1976). A benzhydrylamine resin is commercially available from Beckman Instruments, Inc., Bioproducts Department, Palo Alto, Ca.

The preparation of the hydroxymethyl resin is described by Bodanszky et al., Chem. and Ind. (London), 38, 1597-98 (1966). The preparation and use of the chloromethyl resin and the hydroxymethyl resin is described by Stewart et al., "Solid Phase Peptide Synthesis" [Freeman and Co., San Francisco (1969)]pp. 1-13 and 27-28. Stewart et al., Ibid., provides a full discussion of solid phase synthesis methods, procedures and apparatus.

The benzhydrylamine resin is particularly useful in the preparation of those pentapeptides of Formula I in which X is an amino group because cleavage of the completed pentapeptide from the resin yields the terminal amide directly. The ester linkage formed in the use of the chloromethyl or hydroxymethyl resins may also be cleaved, by ammonolysis with a solution of methanol saturated with ammonia, to yield the peptide amide directly. If, however, ammonolysis of the peptide from the resin is unsatisfactory, the peptide may be first cleaved from the resin by transesterification with methanol and triethylamine and then converted to the amide in solution.

The benzhydrylamine resin may be cleaved from the protected pentapeptide by treatment with hydrofluoric acid in anisole, which also removes the tert-butyloxycarbonyl (t-Boc) amino protecting group and side-chain protecting groups, such as the benzyl group. Thus, cleavage of the completed peptide from the resin support and deprotection can be accomplished in one step, as preferred, by this choice of amino and hydroxyl protecting groups in combination with the benzhydrylamine resin.

The α-amino- and hydroxy-protected D-serine is coupled to the benzhydrylamine resin with the aid of a carboxyl group activating compound such as diisopropylcarbodiimide (DIC). Following this coupling, the α-amino protecting group is removed by, for example, trifluoroacetic acid in methylene chloride, trifluoroacetic acid alone, or hydrochloric acid in dioxane. The deprotection is carried out at temperatures between about 0° C. and room temperature. After removal of the α-amino protecting group (but leaving the side-chain protecting group intact), the remaining α-amino protected and side-chain protected amino acids are coupled in step-wise fashion according to the above protocol in order to obtain a compound of Formula I. However, an alternative to adding each protected amino acid separately is to add two or more protected amino acids which have been separately coupled (usually as commercially available reagents) to the solid phase reactor for coupling. Each protected amino acid or amino acid sequence is introduced into the solid phase reactor in about a six-fold excess and the coupling is carried out in a medium of dimethylformamide:-methylene chloride (1:1) or in either of these solvents alone. In cases where incomplete amino acid coupling is found to have occurred, the coupling procedure is repeated before removal of the α-amino protecting group for the subsequent coupling. The success of the amino acid coupling reaction at each stage of the synthesis is monitored by the ninhydrin reaction as described by E. Kaiser et al., Analyt. Biochem. 34, 595 (1970).

Numerous α-amino protecting groups useful in solid-phase and non-solid-phase peptide synthesis are well-known in the art. Among the classes of α-amino protecting groups are (1) acyl, (2) aromatic urethan, (3) aliphatic urethan, (4) cycloalkylurethane, (5) thio urethan, (6) alkyl, and (7) trialkylsilane. The aromatic urethane type α-amino protecting group tert-butyloxycarbonyl (t-Boc) is particularly preferred for the preparation of compounds of Formula I. The t-Boc protecting group is conveniently removed using trifluoroacetic acid in methylene chloride, without cleaving the peptide from the support resin.

The use of the various α-amino protecting groups enumerated above for peptide synthesis, including reagents for removal of such groups, is well-known in the art, and is described in Schroeder and Lubke, *The Peptides*, Vol. 1, Chapter 1, Academic Press (1965) and in McOmie, Ed., *Protective Groups In Organic Chemistry*, Chapter 2.1, Plenum Press (1973).

The side-chain hydroxyl group of serine is preferably protected with a benzyl group. The hydroxyl group of tyrosine is preferably protected with a 2,6-dichlorobenzyl group. Such groups are chosen because they are not removed under the conditions used to remove the α-amino protecting groups, but are removable under the same conditions used to cleave the completed peptide from the resin support. Other suitable hydroxyl protecting groups and their use are known in the art and are discussed particularly in Stewart, supra, 13-15, with respect to hydroxymethyl and chloromethyl resin supports.

Methods of purifying the crude pentapeptide product are well-known in the art and are described, for example, in Stewart, supra, pp. 49-52.

Also contemplated by this invention are the salts of the pentapeptide of Formula I with non-toxic, pharmaceutically acceptable acids. Suitable acids, both organic and inorganic, will be readily apparent to one skilled in the art, for example: hydrochloric, hydrobromic, sulfonic, phosphoric, maleic, acetic, citric, benzoic, succinic, malic, ascorbic, and the like. The salts are prepared and isolated by conventional methods.

The symbols used for representing the amino acid residues in Formula I and in the other formulae employed herein are defined according to the IUPAC-IUB Commission on Biochemical Nomeclature Recommendations (1971), Archives of Biochemistry and Biophysics, 150, 1-8 (1972).

The pentapeptides of Formula I, or a pharmaceutically acceptable salt thereof, exert an analgesic effect when administered peripherally as demonstrated in mice using the phenylbenzoquinone-induced writhing test. The procedure is a modification of the method described by Siegmund and Cadmus, Proc. Soc. Exp. Biol. Med., 95, 729-731 (1957), which is used to evaluate both narcotic and non-narcotic analgesics. In this procedure, the analgic activity of a compound is assessed by its ability of completely inhibit phenylbenzoquinone (PBQ)-induced writhing. Laboratory mice of either sex, weighing 18-27 g. are used in groups of ten as test subjects. The test compound is administered first in an initial dose determined by the potency of the class of compounds and the route of administration. The test is run first in one group of mice at a relatively high dose to establish significant analgesic activity [see (1) in Table I]. When analgesic activity is observed in four or more of this group, a second test is run on at least three groups of mice to determine the most appropriate dose/time response to use in the subsequent dose response test [see (2) in Table I]. Finally, the $ED_{50}$ dose is determined by administering different doses to several groups of mice and observing their reaction during the time interval established by the dose/time test [see (3)-(9) in Table I]. Note that the time interval is designated by the median time of the chosen response observation period (e.g. 15, 30, or 45 minutes). In testing each group of mice according to the above protocol, all mice in the group first are administered the selected dose of the test compound solution. Five minutes prior to the observation period (viz. at 5, 20, or 35 minutes after subcutaneous administration of the test compound of at 20, 50, or 80 minutes after oral administration of the test compound) all mice in the group receive 0.25 ml., intraperitoneally, of the writhing agonist (i.e. 0.02% solution of PBQ). At the chosen time interval, the group of mice is observed for a period of ten minutes for writhing.

When administered subcutaneously according to this procedure, the compound of Example 1 N—Me—Tyr—D—Met—Gly—N—Me—Phe—D—Ser—$NH_2$, acetate, elicited analgesic activity as set out in Table I below:

TABLE I

| | Dose mg/kg. | No. Analgesic Total No. Tested (time-minutes) | | |
|---|---|---|---|---|
| | | 15 | 30 | 45 |
| (1) | 10.0 | 10/10 | | |
| (2) | 0.1 | 4/10 | 3/10 | 1/10 |
| (3) | 0.032 | 0/10 | | |
| (4) | 0.056 | 3/10 | | |
| (5) | 0.1 | 2/10 | | |
| (6) | 0.178 | 6/10 | | |
| (7) | 0.316 | 5/10 | | |
| (8) | 0.56 | 4/10 | | |
| (9) | 1.00 | 8/10 | | |

$ED_{50} = 0.33$ mg/kg.

The results in Table I show that the $ED_{50}$ was 0.33 mg/kg. and that the test compound, administered subcutaneously, elicited analgesia at 15 minutes after injection of the PBQ in 8 of 10 animals at a dose of 1.0 mg/kg. and in 10 of 10 animals at a dose of 10 mg/kg.

Another standard test for determining analgesic activity of a test compound is the rat-tail flick method of D'Amour and Smith which may be administered as described by Belluzzi et al., Nature, 260, 625 (1976). In this procedure, the analgesia elicited by the test compound is generally compared with that of a known analgesic, such as morphine sulfate. A variation of this procedure utilizes a hot plate instead of a heat lamp as the pain stimulant.

Evidence of the opiate-like analgesic activity of a test compound may be obtained by use of an in vitro opiate receptor assay. Such a procedure, utilizing a rat brain homogenate, is described by Chang et al., Life Sciences, 18, 1473-82 (1976). In this procedure, a fasted male Charles River CD rat, 190-290 g., is killed with a guillotine after carbon-dioxide anesthesia, and the brain is rapidly removed. After the cerebellum is excised, the brain is homogenized in 100 vol. (usually 150 ml.) iced 0.05 M Trizma buffer (pH 7.4 at 25°) 0.1 M in sodium chloride in a Brinkman Polytron for 1 min. at setting 3. The homogenate is centrifuged at 49,500 g for 15 min. (Sorvall SS-34 rotor at 19,500 rpm) in 50 ml. propylene tubes. The supernatant is decanted, and the pellets are resuspended in iced buffer to the original volume by use of a motor driven pestle tissue grinder. The homogenate is centrifuged again and resuspended in 10 ml. iced buffer.

In the assay, 0.10 ml. of this iced homogenate is added to 12×75 mm. plastic tubes, and the following protocol is observed:

| | 3H-Naloxone (0.05 ml. of 1.3 × $10^{-8}$M) | Sample (0.05 ml.) | Morphine (0.05 ml. of 2 × $10^{-2}$M) | Buffer ml. |
|---|---|---|---|---|
| Control (6 tubes) | + | − | − | 0.35 |
| Sample (5 conc.) (4 tubes) | + | + | − | 0.30 |
| Carrier | + | − | + | 0.30 |

| 3H-Naloxone (0.05 ml. of $1.3 \times 10^{-8}$M) | Sample (0.05 ml.) | Morphine (0.05 ml. of $2 \times 10^{-2}$M) | Buffer ml. |
|---|---|---|---|
| (6 tubes) | | | |

Homogenates and samples ae equilibrated at room temperature for 5 minutes before adding 0.05 ml. 3 H-naloxone solution to give a total volume of 0.50 ml. for all tubes.

The assay tubes are hand-shaken every 15 min. for an incubation time of 60 min. at 0° C. The contents are filtered under reduced pressure through Whatman glass-fiber circles (GF/B, 2.4 cm. dia.). The filters are washed twice with 8 ml. cold buffer, placed in scintillation vials, and 12 ml. of Hydromix (Yorktown Research) are added to each vial. The vials are hand-shaken immediately, after 30 min., at the end of the day, stored overnight, hand-shaken, and radioactivity is determined by liquid-sintillation spectrometry.

The assay is calculated as follows:

Control (specific + non-specific binding) − Carrier (non-specific binding)

Sample (specific + non-specific binding) − Carrier net control = 100% binding     net sample $$100 \times \frac{\text{net sample}}{\text{net control}} = \% \text{ control binding}$$

The data is plotted as % control binding vs. log concentration sample to obtain the concentration that displaces 50% of the 3 H-naloxone ($ED_{50}$). Comparisons are made with a standard such as morphine to obtain relative displacement potencies. Assays are run twice for each sample on different days. Displacement is exhibited by both opiate agonists and antagonists.

When tested according to this procedure, the compound of Example I, N—Me—Tyr—D—Met—Gly—N—Me—Phe—D—Ser—NH$_2$, acetate, gave the results shown in Table II below:

Table II

| Sample | $ED_{50}$(M) | Relative Displacement Potency |
|---|---|---|
| Morphine | $3.75 \times 10^{-7}$ | 1.0 |
| Example 1 Compound | $2.63 \times 10^{-8}$ | 14 |

Such results demonstrate that the compound of Example I has in excess of ten times the opiate receptor binding capacity of morphine.

Another procedure used to determine opiate receptor binding properties of test compounds utilizes an electrically simulated isolated guinea pig ileum preparation as described by Kosterlitz et al., Brit. J. Pharmacol. Chemotherap., 33, 266–276 (1968). A similar procedure utilizes a mouse vas deferens preparation as the test object.

In employing the compounds of the invention, the particular dose to be administered will vary somewhat depending on the degree of analgesia desired, the particular animal being treated, and the particular compound of the invention being employed. In general, an intravenous dose of from 0.025 to 2.5 mg/kg. or a subcutaneous dose of from 0.25 to 25 mg/kg. will produce the desired effect. Preferably, analgesic therapy is initiated by administering a low dose of compound, the dosage thereafter being increased in succeeding administrations until the desired degree of analgesia is obtained. The precise dose for production of a desired effect will be readily determined by one skilled in the art.

The following example further illustrates the best mode of carrying out the invention.

EXAMPLE 1

N-Methyl-Tyrosyl-D-Methionyl-Glycyl-N-Methyl-Phenylalanyl-D-Serinamide . Acetate To a 200 ml. reaction vessel added 30.0 g. of benzhydrylamine resin (9 m moles free amine content). The resin was then treated in the following manner:

1. methylene chloride (three times)
2. 5 minute prewash with 30% trifluoroacetic acid-methylene chloride (v/v) containing 0.5% dithioerythritol
3. 25 minute treatment with the above described trifluoroacetic acid
4. methylene chloride (three times)
5. 10 minute treatment with triethylamine-dimethylformamide 15% (v/v)
6. dimethylformamide (three times)
7. methylene chloride (three times)

A contact time of 2 minutes is allowed for each wash unless otherwise indicated.

The resin is gently stirred with t—Boc—O—Bzl—D—Ser and 1-hydroxy-benzotriazole (HOBT) in 50% methylene chloride-dimethylformamide (60 m moles t—Boc—O—Bzl—D—Ser and 60 m moles HOBT). Following the addition of the above reagents the mixture was treated with 63 mm. of diisopropylcarbodiimide (the DIC was added in two equal portions over 30 minutes). After stirring overnight the peptideresin was washed successively with dimethylformamide (twice), 12% triethylamine-dimethylformamide (once) and methylene chloride (thrice). To test for completeness of reaction the peptide-resin was subjected to a ninhydrin color test following the procedure of E. Kaiser et al., Analytical Chemistry, 34, 595 (1970).

The deprotection of the attached amino acid was carried out as described in steps (2) through (7) above.

The following amino acid residues were then introduced consecutively: t—Boc—N—Me—Phe (60 m moles, 60 m moles HOBT and 63 m moles DIC), t—Boc—Gly (60 m moles, 60 m moles HOBT and 63 m moles DIC). After the completion of the coupling of t—Boc—Gly the resin was divided and the synthesis continued on a one-third portion of the resin. The following amino acid residues were introduced: t—Boc—D—Met (20 m moles, 20 moles HOBT and 21 m moles DIC), t—Boc—N—Me—O—2,6—Cl—Bzl—Tyr (20 m moles, 20 m moles HOBT and 21 m moles DIC). The resulting washed pentapeptide resin was dried in vacuo to yield 18 g.

The above described pentapeptide resin (18 g.) was treated in vacuo with anhydrous liquid hydrogen fluoride (200 ml.) and anisole (20 ml.) at 0° for 1 hour. The hydrogen fluoride and anisole were removed under reduced pressure and the residue treated with AG-3-X4 A ion exchange resin (acetate form) for 30 min., filtered and lyophilized, yielding 7.0 g. of the crude product.

Purification and Characterization of N-Methyl-Tyrosyl-D-Methionyl-Glycyl-N-Methyl-Phenylalanyl-D-Serinamide . Acetate The above titled crude product was purified as follows: 1.5 g. of material is dissolved in a minimum amount of 2 N acetic acid and applied to a column (2.5×200 cm.) of Saphadex G-10 in 2 N acetic acid. The column was eluted with 2 N acetic acid and 15 ml. fractions collected. The column effluent was monitored at 254 nm. Fractions 39-48 were combined, concentrated and further purified by applying the material in a small volume of upper phase B:A:W, 4:1:5 (n-butanol:acetic acid:water) onto a column (2.5×150 cm.) of Sephadex G-25 medium previously equilibrated with lower phase of the above system and then upper phase. The column was eluted with upper phase B:A:W and 11 ml. fractions collected. The effluent was monitored as above. Tubes 38-53 were shown to be homogenous by thin layer chromatography systems 7:7:6 (isoamyl alcohol:pyridine-water); $R_f=0.75$ and 4:1:5 (butanol:acetic acid: water); $R_f=0.40$. Thin layer chromatograms were visualized with ninhydrin and chlorine peptide reagent. Amino acid analysis following methane sulfonic acid hydrolysis gave the following ratios: Ser 0.95; Gly 1.00; Met 0.88. The structure of the compound was also confirmed by proton NMR. $[\alpha]_D^{25}=+19.12$ (0.625% in 1% acetic acid).

What is claimed is:

1. A pentapeptide of the formula:

$$R^1-N-H-Tyr-N-R^2-D-Met-Gly-N-R^3-Phe-N-R^4-D-Ser-X$$

wherein
$R^1$ is hydrogen, methyl, ethyl, propyl, 2-methyl-2-pentenyl, 2-methyl-1-pentenyl, methylcyclopropyl, or methylcyclobutyl;
$R^2$, $R^3$, and $R^4$ are, independently, hydrogen or methyl; and
X is an amino group, $-OR^5$, or $-CH_2OR^5$ where $R^5$ is hydrogen or an alkyl group containing 1 to 6 carbon atoms;
or a pharmaceutically acceptable salt thereof.

2. A pentapeptide of claim 1 wherein $R^3$ is methyl.

3. A pentapeptide of claim 1 wherein $R^1$ is methyl, ethyl, propyl, 2-methyl-2-pentenyl, 2-methyl-1-pentenyl, methylcyclopropyl, or methylcyclobutyl; and $R^2$ and $R^4$ are hydrogen.

4. A pentapeptide of claim 1 wherein X is an amino group.

5. A pentapeptide of claim 1 wherein $R^3$ is methyl and X is an amino group.

6. The pentapeptide of claim 1 wherein is N-methyl-tyrosyl-D-methionylglycyl-N-methyl-phenylalanyl-D-serinamide.

* * * * *